(12) United States Patent
Naghavi et al.

(10) Patent No.: US 8,246,548 B2
(45) Date of Patent: Aug. 21, 2012

(54) ISCHEMIC CONDITIONING FOR IMPROVED ATHLETIC PERFORMANCE

(76) Inventors: Morteza Naghavi, Houston, TX (US); Albert Andrew Yen, Pearland, TX (US); Haider Ali Hassan, Houston, TX (US); David S. Panthagani, Houston, TX (US)

( * ) Notice: Subject to any disclaimer, the term of this patent is extended or adjusted under 35 U.S.C. 154(b) by 0 days.

(21) Appl. No.: 13/229,738

(22) Filed: Sep. 11, 2011

(65) Prior Publication Data
US 2011/0319732 A1 Dec. 29, 2011

Related U.S. Application Data

(63) Continuation of application No. 12/323,392, filed on Nov. 25, 2008.

(60) Provisional application No. 60/989,946, filed on Nov. 25, 2007.

(51) Int. Cl.
*A61B 5/02* (2006.01)
*A61B 17/00* (2006.01)

(52) U.S. Cl. ........ 600/500; 600/481; 600/483; 606/201; 606/202

(58) Field of Classification Search .......... 600/150–152, 600/301, 309, 323, 324, 438, 481, 483, 490, 600/492–495, 499, 504; 606/201, 202, 157; 606/158; 601/84; 482/13
See application file for complete search history.

(56) References Cited

U.S. PATENT DOCUMENTS

| | | | | |
|---|---|---|---|---|
| 5,571,075 A * | 11/1996 | Bullard | | 601/152 |
| 6,702,720 B2 * | 3/2004 | Dardik | | 482/13 |
| 6,962,599 B2 * | 11/2005 | Hui | | 606/202 |
| 7,048,702 B2 * | 5/2006 | Hui | | 601/152 |
| 7,314,478 B2 * | 1/2008 | Hui | | 606/202 |
| 7,338,410 B2 * | 3/2008 | Dardik | | 482/13 |
| 7,717,855 B2 * | 5/2010 | Caldarone et al. | | 600/496 |
| 8,114,026 B2 * | 2/2012 | Leschinsky | | 600/490 |
| 2005/0070405 A1 * | 3/2005 | Egger | | 482/78 |
| 2008/0139949 A1 * | 6/2008 | Caldarone et al. | | 600/490 |
| 2008/0222769 A1 * | 9/2008 | Natonson et al. | | 2/70 |
| 2009/0287243 A1 * | 11/2009 | Greennberg | | 606/202 |
| 2010/0292619 A1 | 11/2010 | Redington | | |

OTHER PUBLICATIONS

Patricia C.E. De Groot, Ischemic preconditioning improves maximal performance in humans, Eur J Appl Physiol (2010) 108: 141-146, The Netherlands.
M. Wernbom, J. Augustsson, Inchemic strength training: a low-load alternative to heavy resistance exercise?, Scand J Med & Sci Sports, 2008, 18: 401-416.

(Continued)

*Primary Examiner* — Navin Natnithithadha
(74) *Attorney, Agent, or Firm* — David McEwing P.C.

(57) ABSTRACT

Methods for ischemic conditioning treatments of a chronic medical condition are provided. Baseline disease-related parameters of a patient with a chronic medical condition are measured. Ischemia is induced in the patient by occluding and releasing arterial flow in one or more extremities of the patient. Post-ischemia parameters in the patient are measured. The baseline and post-ischemia parameters are compared to provide an assessment of an ischemic conditioning treatment of a chronic medical condition. The repeated, scheduled delivery of ischemic conditioning provides a beneficial, therapeutic effect on the chronic medical condition. Also provided is a device for pulse oximetry during periods of absent or low pulsatile blood flow including an artificial pulse generator as well as the use of said device in assessment of ischemic conditioning.

18 Claims, 4 Drawing Sheets

OTHER PUBLICATIONS

Jack A. Loeppky, Burke Gurney, Effects of ischemic training on leg exercise endurance, JRRD, Jul./Aug. 2005, vol. 42, No. 4, p. 511-522.

Minoru Shinohara, Motoki Kouzaki, Efficacy of tourniquet ischemia for strength training with low resistance, Eur J Appl Physiol, 1998, 77: 189-191.

* cited by examiner

ISCHEMIC CONDITIONING FOR IMPROVED ATHLETIC PERFORMANCE

CROSS REFERENCE TO RELATED APPLICATIONS

This application is a continuation of application Ser. No. 12/323,392 filed Nov. 25, 2008 entitled "Methods and Apparatus for Repeated Ischemic Conditioning Treatment of Hypertension and Similar Conditions" which is incorporated by reference in its entirety herein. This application claims priority based on U.S. Provisional Application No. 60/989,946 filed Nov. 25, 2007, the disclosure of which is incorporated herein by reference in its entirety.

FIELD OF THE INVENTION

This invention relates to methods and apparatus for ischemic conditioning to prevent, reduce, and/or treat certain chronic medical conditions, in particular, hypertension. Ischemic conditioning is implemented using noninvasive or invasive arterial occlusion and skin compression, and combinations thereof. More specifically, this invention relates to the treatment of high blood pressure (hypertension) using repeated ischemic conditioning.

BACKGROUND OF THE INVENTION

Without limiting the scope of the invention, its background is described in connection with treatment of hypertension and other chronic medical conditions including but not limited to peripheral arterial disease (PAD), Raynaud's syndrome, coronary heart disease (CHD), coronary artery disease (CAD), diabetes, pulmonary hypertension (PH), and connective tissue disorders.

By definition, chronic conditions are present when there is a persistent or lasting medical problem. For example, hypertension is considered to be present when there is persistent elevation of either systolic blood pressure or diastolic blood pressure, or when a patient has been placed on antihypertensive medication because of persistently elevated blood pressure (regardless of the current blood pressure level). The blood pressure level correlates directly with the magnitude of risk for clinical sequelae such as premature death, stroke, myocardial infarction, congestive heart failure, renal insufficiency, dementia, and peripheral vascular disease. As a result, numerous antihypertensive drugs have been developed to treat elevated blood pressure. Well known classes of prevalent anti-hypertensives include Angiotensin-Converting Enzyme (ACE) Inhibitors, Alpha$_1$ Antagonists, Angiotensin II (AT$_1$) Receptor Antagonists, Blockers, Calcium Antagonists, Central Adrenergic Inhibitors, Direct Vasodilators, and Diuretics.

Pharmacological blood pressure lowering reduces the risk of premature cardiovascular morbid and fatal events as well as all-cause mortality. Antihypertensive drug therapy has also been shown to prevent the gradual progression of mild hypertension to more severe elevations of blood pressure. The prevalence of pressure-related target-organ damage (i.e., elevated serum creatinine, left ventricular hypertrophy) is also greater at higher blood pressure levels. Hypertensives (individuals with chronic hypertension) with pressure-related target-organ damage manifest a several-fold higher risk for pressure-related clinical complications at a given blood pressure level compared to hypertensives with similar levels of pressure without target-organ damage. Early treatment of hypertension favorably impacts long-term clinical risk, in part, by preventing the development of pressure-related target organ damage. However, hypertensive agents can cause hazardous side effects related to the dosage of medicine, the dangers of a rapidly decreasing blood pressure, and ischemic infarction of organ tissues (e.g. angina pectoris, myocardial infarction, transient ischemic attack, and stroke).

Similarly, other chronic conditions such as peripheral arterial disease and diabetes are also treated by pharmacological therapies. Several other important therapeutic principles are considered in treating patients of chronic conditions. In most cases, there is minimal to no value in rapid pharmacological control of a persistent or recurring condition. Rather, the goal for the vast majority is to prescribe a combination of appropriate lifestyle modifications (e.g. weight loss, dietary restriction, and increased physical activity) plus the lowest doses of drug(s) that allow for normalization over the long term. Further, many medications have dose-related side effects. Drug acquisition costs also usually increase at higher dose levels. In certain instances, cost is a major barrier to patient compliance with prescribed drug therapies. However, even the other non-invasive lifestyle approaches to chronic disease management can be tempered with side effects and ineffectiveness. For example, regular exercise is known to lower blood pressure in healthy individuals by inducing ischemia but also is problematic because it causes an increase in heart rate that may not be tolerated well by some individuals. Further, exercise, diet, and weight loss programs are all well known to suffer problems of compliance.

Accordingly, what are needed are further methods and apparatus for the management and treatment of chronic medical conditions, in particular hypertension, as well as methods and apparatus for applying ischemic conditioning to improved athletic performance.

BRIEF SUMMARY OF THE INVENTION

The present invention provides methods and apparatus for utilizing the protective effects of repeated, noninvasive applications of ischemic conditioning to treat long term chronic health conditions. In one embodiment of the invention, repeated ischemic conditioning is applied to confer pharmacologic-like and exercise-like therapeutic effects by increasing the vasodilative capacity of the vasculature in the limbs in order to positively affect a vascular condition.

In one embodiment of the invention, the patient is treated for hypertension, peripheral arterial disease, Raynaud's syndrome, coronary heart disease (CHD), coronary artery disease (CAD), heart failure, pulmonary hypertension (PH), diabetes, and/or connective tissue disorders. In one embodiment of the invention the vascular condition is a starting vascular condition of an athlete and the program of ischemic conditioning is administered on a repeated, scheduled basis adapted to improved endurance and athletic performance.

In one embodiment of the invention, treatment is effected using transient ischemia. In other embodiments, treatment is complemented using heat, including, for example, photo thermal energy.

In one embodiment, conditioning is effected by transiently and repeatedly administering the treatment to at least one limb, or part thereof, for treatment or prevention of hypertension. The ischemia conditioning treatment in one embodiment is transiently and repeatedly applied according to a schedule that is tailored to the medical and psychosocial needs of the individual patient. In accordance with one embodiment, the program of ischemic conditioning includes at least 1 cycle of from 1 to 20 minutes of occlusion on at least one extremity, at least 2-4 times per week. In one embodiment, the program of ischemic conditioning includes at least 1 cycle of from about 2 to about 5 minutes of occlusion. The program can be adapted to the patient by monitoring the relationship between different administration protocols and the blood pressure of the patient with a goal towards maximizing the lowering of blood pressure in the individual patient. In one version of the invention, the program of ischemic conditioning includes at least 2 cycles of about 2 to about 5 minutes of occlusion followed by about 2 to about 5 minutes of release of an extremity at least 2-4 times per week.

In one embodiment of the invention, the ischemic conditioning is applied to one or more extremities using an external cuff system for arterial occlusion. Alternatively or in addition, the ischemic conditioning is applied to one or more extremities using external pressure to the skin using a pressurizable garment.

In other embodiments, the ischemic conditioning includes a measurement aspect comprising one or more of determining a DTM response and a determination of blood oxygen saturation during ischemia using artificial pulse together with oximetry to improve the ischemic conditioning treatments. The artificial pulse may be generated by mechanical actuation. In some version of the invention, the mechanical actuation is effected by pulsating fluid pressure in a cuff to cause mechanical disturbance of arterial blood, repetitive, external electromechanical actuation, or repetitive, self-induced physical motion. Alternatively or in addition, the artificial pulse may be generated by external non-mechanical optical illumination utilized to imitate an absorption pattern of a pulsatile blood flow signal by oscillating an intensity of a light source of either a single or multiple wave length. Assessment of the progress of the ischemic conditioning treatment may include measuring one or more baseline hemodynamic parameters of a patient, applying an ischemic conditioning treatment in the patient by occluding and releasing arterial flow in one or more extremities of the patient on a scheduled, repeated basis, measuring post-ischemia parameters in the patient, and comparing the baseline and post-ischemia parameters to provide an assessment of the ischemic conditioning treatment over time.

In one embodiment wherein the ischemia conditioning treatment includes induced ischemia, the induced ischemia is sufficient to induce reactive hyperemia in the distal extremity including both hands, both feet, or both hands and feet, and/or portions thereof. The method may be complemented by instructing a schedule of hand and/or foot exercises to the patient.

In one embodiment wherein the ischemia conditioning treatment includes induced ischemia, continued monitoring by pulse oximetry of the induced ischemia, in the absence of pulsatile flow, is enabled by the creation of artificial pulsatile signals. The artificial pulsatile signals can be generated by either external mechanical actuation that causes oscillatory displacement of blood or external non-mechanical optical illumination.

In one embodiment of the invention, a synergistic combination of physical exercise and ischemic conditioning is provided for prevention and treatment of hypertension. In another embodiment, methods and apparatus for treatment of intermittent claudication (a symptom of peripheral arterial disease) is provided using ischemic conditioning to increase dilative capacity and metabolic efficiency of conditioned areas. As a consequence, patients with intermittent claudication are enabled to walk longer distances and/or suffer less pain when walking the same distance.

In one embodiment employing induced ischemia as a conditioning treatment, the induced ischemia is transiently and repeatedly induced in at least one limb or portion thereof of a patient according to a schedule of vascular occlusions. Alternatively, or in addition to other conditioning treatments, in one embodiment, heat sufficient to induce vasodilation is applied to at least one distal extremity of the patient. In other embodiments, pharmacotherapy is initiated in conjunction with ischemic conditioning and/or heat treatments. The conditioning pharmacotherapy is effected by administration with one or more of the group of vasodilators, anti-oxidants, anti-inflammatory and anesthetic compounds and nitric oxide (NO) donors, precursors and agonists. In one embodiment, the pharmacotherapy is administered systemically.

In one embodiment, an apparatus is provided for transiently inducing ischemia in a peripheral vascular area of a patient, the apparatus including a plurality of releasable compressing elements, each adapted to reduce or occlude flow of blood to at least a portion of an extremity of the patient. The releasable compressing elements may comprise bands dimensioned to be tightened around at least one extremity such as an arm and/or leg to occlude flow of blood to at least a portion of the hands and/or feet. Alternatively, the releasable compressing elements may comprise inflatable compression suits, mittens, socks, stockings, gloves and/or full body suits.

In one embodiment of the invention, apparatus for transiently and repeatedly inducing ischemia in a peripheral vascular area of a patient includes use of a plurality of releasable bands, each adapted to occlude blood supply to at least a hand or foot of the patient when tightened or inflated. As used here, the term band includes cuffs such as inflatable blood pressure type cuffs. The apparatus may be manual in operation or may be automated such as with a control device for controlling compression and release of elements in accordance with a schedule. In one embodiment the apparatus includes a programmable computer for inducing ischemia in accordance with a schedule. In one embodiment the apparatus further includes a pump in operable communication with the releasable compressing elements, wherein the action of the pump results in tightening or inflation by filling of the releasable compressing elements. The apparatus may further include one or more heating mechanisms for intermittent heating at least one hand or foot.

BRIEF DESCRIPTION OF THE INVENTION

Figure 1:
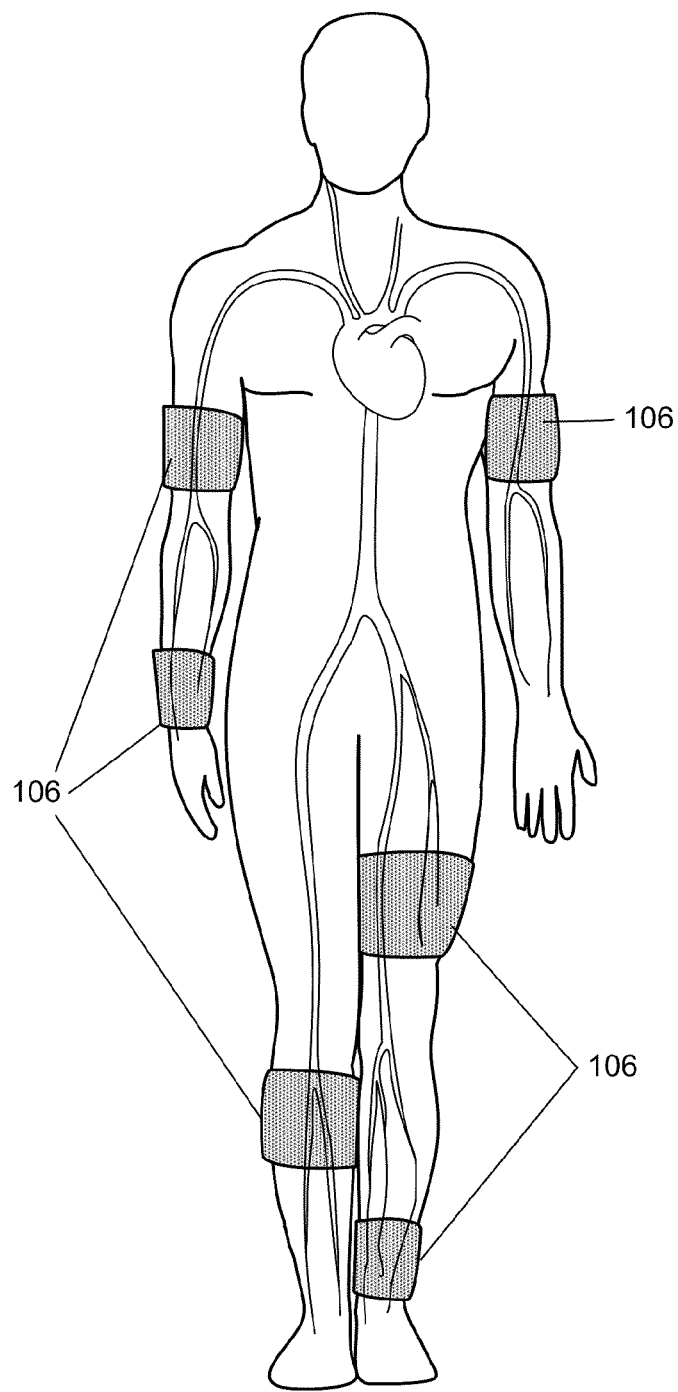
FIG. 1 depicts several locations for placement of occlusive bands or cuffs for inducing transient intermittent ischemia.

Disclosed herein is a novel method of conditioning the vasculature of patients in order to reduce the potential for complications that occur with frequency as a consequence of chronic medical conditions, particularly hypertension, but also Raynaud's syndrome, coronary heart disease (CHD), coronary artery disease (CAD), peripheral arterial disease (PAD), diabetes, pulmonary hypertension (PH), and/or connective tissue disorders. In one embodiment, treatment of these chronic conditions is provided by repeated treatment or conditioning by using transient ischemia or hypoxia in order to increase the vasodilative capacity of the vasculature. In other embodiments, treatment is provided by application of heat at levels sufficient to induce peripheral vasodilatation and increase cardiac output and vasodilative capacity. Treatment may be augmented using pharmacologic interventions including blood pressure lowering drugs. In effect, the methods and apparatus of the present invention emulate the positive effects of exercise on the vasculature in a population that has reduced capacity for exercise due to their chronic disease status.

The invention relies, at least in part, on physiologic reactions to ischemia. Brief periods of ischemia (a local shortage of oxygen-carrying blood supply) in biological tissue, render that tissue more resistant to subsequent ischemic insults through several mechanisms including through increased vasodilative capacity. Ischemic conditioning exerts protection and appears to be a ubiquitous endogenous protective mechanism at the cellular level that has been observed in the heart of humans and every animal species tested. This protection has also been seen in organs such as the liver, kidney, gut, skeletal tissue, urinary bladder and brain. In fact, ischemic conditioning can have an effect on any proliferative tissue, e.g. skin, hair, and bone marrow.

The therapeutic and protective effects of ischemic conditioning may be mediated by signal transduction changes to tissues. With respect to cardiac tissue, the current paradigm suggests that nonlethal episodes of pre-ischemia reduce the infarct size that results from subsequent total blockage of arterial blood supply. Ischemic conditioning has been found to lead to the release of certain substances, such as adenosine and bradykinin. These substances bind to their G-protein-coupled receptors and activate kinase signal transduction cascades. These kinases converge on the mitochondria, resulting in the opening of the ATP-dependent mitochondrial potassium channel. Reactive oxygen species are then released. Thus, additional protective signaling kinases can be activated, such as heat shock inducing protein kinase C.

Further, the signaling kinases mediate the transcription of protective distal mediators and effectors, such as inducible nitric oxide synthase, manganese superoxide dismutase, heat-stress proteins and cyclo-oxygenase 2, which manifest 24-72 hours after infarction to provide late protection. Suggested mechanisms of how these signaling transduction pathways mediate protection, and ultimately reduce infarct size, include maintenance of mitochondrial ATP generation, reduced mitochondrial calcium accumulation, reduced generation of oxidative stress, attenuated apoptotic signaling and inhibition of mitochondrial permeability transition-pore (mPTP) opening. Alternative protective mechanisms of ischemic conditioning that are independent of signal transduction pathways, such as those mediated by antioxidant and anti-inflammatory mechanisms, may provide further protection.

Even further, formation of vascular collaterals is also induced by ischemia and hypoxia of blood vessels. Vascular endothelial growth factor (VEGF) production can be induced in cells that are not receiving enough oxygen. When a cell is deficient in oxygen, it produces the transcription factor Hypoxia Inducible Factor (HIF). HIF stimulates the release of VEGF among other functions including modulation of erythropoiesis. Circulating VEGF then binds to VEGF receptors on endothelial cells and triggers a tyrosine kinase pathway leading to angiogenesis.

Ischemic conditioning has been shown to produce tolerance to reperfusion damage from subsequent ischemic damage. One physiologic reaction to local ischemia in normal individuals is reactive hyperemia to the previously ischemic tissue. Arterial occlusion results in lack of oxygen (hypoxia) as well as an increase in vasoactive metabolites (including adenosine and prostaglandins) in the tissues downstream from the occlusion. Reduction in oxygen tension in the vascular smooth muscle cells surrounding the arterioles causes relaxation and dilation of the arterioles and thereby decreases vascular resistance. When the occlusion is released, blood flow is normally elevated as a consequence of the reduced vascular resistance.

Perfusion of downstream tissues is further augmented by flow-mediated dilation (FMD) of larger conduit arteries, which acts to prolong the period of increased blood flow. As a consequence of the elevated blood flow induced by reactive hyperemia, downstream conduit vessels undergo luminal shear stress. Endothelial cells lining the arteries are sensitive to shear stress and the stress induces in opening of calcium-activated potassium channels and hyperpolarization of the endothelial cells with resulting calcium entry into the endothelial cells, which then activates endothelial nitric oxide synthase (eNOS). Consequent nitric oxide (NO) elaboration results in vasodilation. Endothelium-derived hyperpolarizing factor (EDHF), which is synthesized by cytochrome epoxygenases and acts through calcium-activated potassium channels, has also been implicated in flow-mediated dilation. Endothelium derived prostaglandins are also thought to be involved in flow-mediated dilation.

The therapeutic effects of conditioning are mediated by changes to the vasculature and/or the neurovasculature, as well as anti-inflammatory effects. Nitric oxide (NO) bioavailability may be improved locally. Nitric oxide (NO) has been shown to be involved in cutaneous active vasodilation induced by systemic application of heat on the basis that local inhibition of NO synthase results in inhibition of cutaneous local perfusion while local perfusion of the NO donor, sodium nitroprusside, results in maximum local cutaneous perfusion. Similarly, it has been found that NO mediates vasodilatation in response to local application of heat. Conversely, local cooling induces cold-sensitive afferent nerves to activate sympathetic nerves to release norepinephrine, which leads to local cutaneous vasoconstriction.

Ischemia Preconditioning (IPC) has been found to have remote and systemic protective effects in both human and animal models. Transient limb ischemia (3 cycles of ischemia induced by cuff inflation and deflation) on a contralateral arm provides protection against ischemia-reperfusion (inflation of a 12-cm-wide blood pressure cuff around the upper arm to a pressure of 200 mm Hg for 20 minutes) induced endothelial dysfunction in humans and reduces the extent of myocardial infarction in experimental animals (four cycles of 5 minutes occlusion followed by 5 minutes rest, immediately before occlusion of the left anterior descending (LAD) artery). This phenomenon suggests that ischemic conditioning creates natural therapeutic substances that can have desirable systemic effects.

Recent evidence in a skeletal muscle model has suggested that IPC results in increased functional capillary density, prevention of ischemia/reperfusion induced increases in leukocyte rolling, adhesion, and migration, as well as up-regulation of expression of nNOS, iNOS, and eNOS mRNA in ischemia reperfusion injured tissue. Research has also shown that ischemic preconditioning can result in elevations of heat shock proteins, antioxidant enzymes, Mn-superoxide dismutase and glutathione peroxidase, all of which provide protection from free radical damage.

Although originally described as conferring protection against myocardial damage, preconditioned tissues have been shown to result in ischemia tolerance through reduced energy requirements, altered energy metabolism, better electrolyte homeostasis and genetic re-organization, as well as reperfusion tolerance due to less reactive oxygen species and activated neutrophils released, reduced apoptosis and better microcirculatory perfusion compared to non-preconditioned tissue.

As used herein the term "ischemia" means lowering of baseline blood flow to a tissue. The term "hypoxia" means lowering of arterial $PO_2$. Both ischemia and hypoxia in extremities can be induced by occluding the blood supply upstream of the extremity. By "extremity" it is meant the limbs (arms and legs). By "distal extremity" it is meant the hands and feet, including the digits of the hands and feet. By "regional or local" it is meant, administration to a defined area of the body as contrasted with systemic administration. One embodiment of the present invention employs transient, intermittent ischemia to condition and improve the vasculature of the extremities.

As used herein the phrase "compounds that increase the bioavailability of nitric oxide (NO)" include NO precursors, NO donors and NO agonists. An example of a NO precursor is the essential amino acid substrate L-arginine from which NO is synthesized by the action of nitric oxide synthase (NOS). NO donors, which generate NO via NOS independent processes, include both fast and slow release compounds that typically release NO by either oxidation or reduction. Certain of the NO donor compounds such as nitroglycerin (an organic nitrate), which is enzymatically degraded to generate NO, have been utilized for over a century. Examples of NO donors (sometimes alternatively referred to in art as NO agonists) include the organic nitrates (e.g. glyceryl trinitrate, isosorbide dinitrate), sodium nitroprusside (SNP), syndnonimines (e.g. molsidomine, SIN-1), S-nitrosothiols (e.g. s-nitrosoglutathione), NONOates (e.g. Spermine-NONOate, DETA-NONOate), and hybrid donors such as the nitroaspirins and nicorandil. Certain other compounds that are considered herein to fall within the definition of compounds that increase the bioavailability of NO are compounds, and metabolites thereof, that include nitric oxide chemical structures and are considered to be NO agonists such as for example minoxidil (3-hydroxy-2-imino-6-(1-piperidyl)pyrimidin-4-amine).

Such compounds are considered herein to be NO agonists if their action is the same as NO, such as for example, in opening of membrane potassium channels.

Transient Ischemia for Protection Against Chronic Medical Conditions

In one embodiment of the present invention, intermittent transient ischemia is induced in one or more limbs, or portions thereof, of a patient. The intermittent transient ischemia stimulates and conditions the downstream vasculature and thereby prevents or reduces symptoms of the chronic medical condition.

In accordance with the novel indication of the present invention, in one embodiment the body's own adaptive responses to induced ischemia or hypoxia are harnessed to provide protection against chronic medical conditions such as hypertension, Raynaud's syndrome, coronary heart disease (CHD), coronary artery disease (CAD), peripheral arterial disease, diabetes, pulmonary hypertension (PH), connective tissue disorders, and other chronic diseases involving the vasculature. In accordance with the method disclosed herein, a scheduled series of transient ischemic episodes is administered. The scheduled series of transient ischemic episodes provide protection against the incidence and severity of chronic medical conditions particularly by increasing the dilative capacity in the vasculature of the limbs. Additional beneficial effects include one or more of: increased scavenging of free radicals, reduction in inflammation, and increased functional capillary density.

In one embodiment of the invention, transient ischemia is implemented by cuffs or straps (106) that are secured around one or more of the limbs of the patient, as depicted in FIG. 1. As shown in FIG. 1, the occlusive cuffs or straps can be placed over one or more locations for compression sufficient to occlude blood flow to the hands and or feet. For example, for occlusion of blood supply to the hands, compression can be applied to the upper arm over the brachial artery, the lower arm over the radial and ulnar arteries, or the wrist over the radial artery. For occlusion of blood supply to the feet, compression may be applied to the upper leg over the femoral and deep femoral arteries, or to the lower leg over the tibial arteries. In one embodiment, the cuffs are inflatable and inflation results in sufficient pressure around the circumference of the limb to result in occlusion of the arterial blood supply to the limb. In one embodiment, ischemic conditioning can be administered with cuffs on both arms and both legs.

The duration of ischemia varies by therapeutic targets, but is typically provided for a period from about 1 to about 20 minutes, preferably from about 2 to about 5 minutes, followed by release of the occlusion. Occlusion and release (reactive hyperemia) procedures with different occlusion times are implemented depending on individual tolerance and response to therapy as well as the planned treatment schedule such that a desired distal and or contralateral vascular/neuro/neurovascular function is obtained. Repeated cuff occlusion and release is tailored to improve vasoreactivity (increasing the vasodilative capacity) including by improving nitric oxide bioavailability (reducing destruction or increasing production). This effect can be seen in the same distal extremity as the cuff inflation but is also expected to have neurovascular mediated systemic vasodilation as well.

In one embodiment of the invention, a programmable cuff inflation and deflation device is employed to provide intermittent scheduled transient ischemia. The device can inflate one or more cuffs on one or more body parts at a time. The method induces reactive hyperemia and can mimic the effects of local exercise. The larger the area of ischemia the higher the hyperemia.

Figure 2:
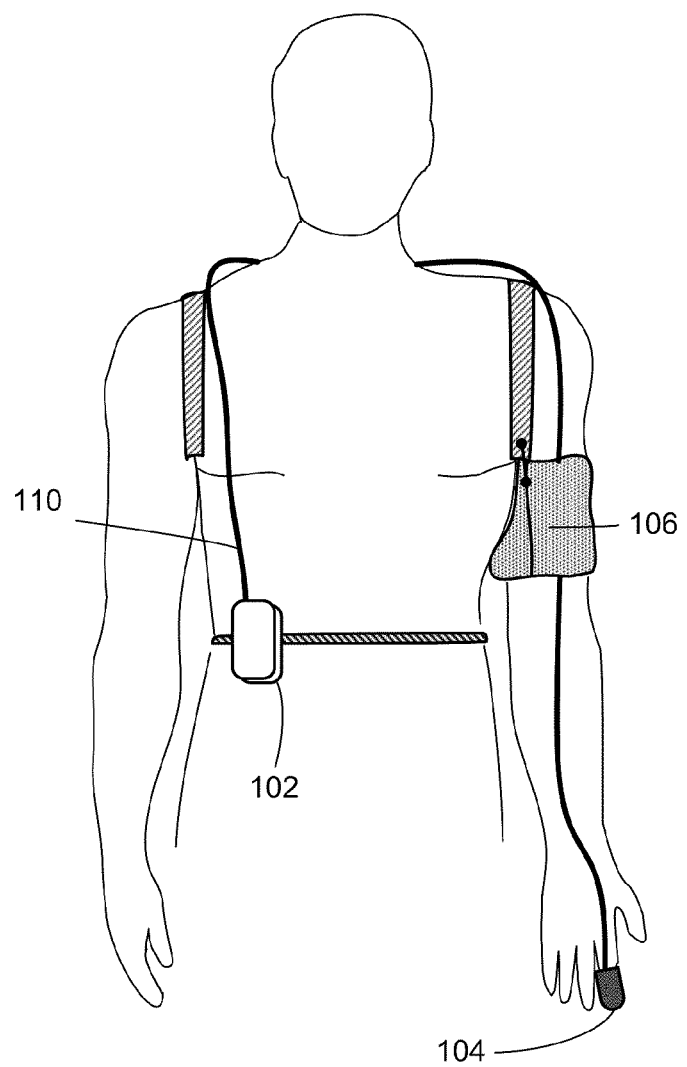
FIG. 2 depicts a halter worn embodiment enabling the patient to wear one or more occlusive cuffs together with a pump and controlling unit for scheduled inflation of the cuff (s).

A portable form of the device is implemented for ambulatory use such as the embodiment depicted in part in FIG. 2. In the embodiment depicted in FIG. 2, one or more occlusive cuffs (106) are in electrical connection via cable (110) with programmable monitor (102) which may be worn anywhere on the body, such as for example on a waist band as depicted. The inclusive cuff can be inflated by an electric pump associated with the programmable monitor, which also can be adapted to record the pattern of occlusion. Alternatively, the cuff(s) can be manually inflated at intervals. In one embodiment, the cuff(s) are manually inflated in response to a signal given by a programmable monitor that instructs inflation and deflation of the inflatable cuff(s). In another embodiment, the monitor instructs manual tightening and loosening of one or more straps in accordance with a programmed schedule.

The duration of ischemia may not have a linear relationship with the effect. After 30 minutes the hyperemia plateaus and the biochemical imprint changes. Desired therapeutic effects are more expected in the first 20 minutes after which the potential harm from the ischemia would have to be weighed against benefits obtained by diminishing chronic complications. In an embodiment, by scheduling separate ischemic conditioning treatments apart from each other in a day (e.g. 3 times a day) can provide maximum therapeutic effect. In an embodiment, conducting ischemic conditioning treatments frequently over extended periods of time (e.g. a day, month, or year) can enhance therapeutic effect. In an embodiment, adjustments to ischemic conditioning regimens can be administered based on assessments of treatment resistance over a period of time and thereby customized to achieve optimal responsiveness in the individual patient. Longitudinal measurement of blood pressure provides a measure of efficacy in the treatment of hypertension.

In one embodiment of the invention, vascular and/or neurovascular and/or peripheral nerve function is determined on a distal extremity to aid in diagnosis, determination of progression and/or management of medical conditions as well as use in assessing the status of the preventive and remediative therapies disclosed herein. In one embodiment, vascular and/or neurovascular function is determined by measuring the vascular or neurovascular response induced by transient blood flow occlusion in the vasculature leading to a distal extremity Vascular or neurovascular reactivity can be monitored by any one of several methods that detect blood flow differences in response to transient blood flow occlusion including inherent skin temperature, clearance of induced skin temperature, tonometry, Doppler ultrasound, laser Doppler flowmetry (such as by a laser Doppler perfusion imaging (LDPI) instrument), plethysmography, iontoporesis, capillometry, and/or changes in magnetic or electromagnetic properties of the tissue.

Inherent skin temperature means the unaltered temperature of the skin. This is in contrast to an induced skin temperature measurement which measures perfusion by clearance or wash-out of heat induced on the skin. Various methods of recording of inherent skin temperature on a finger tip or palm distal to an occlusive cuff are disclosed in Naghavi et al., U.S. application Ser. No. 11/563,676 and PCT/US2005/018437 (published as WO2005/118516) which are incorporated by reference herein. The combination of occlusive means and skin temperature monitoring for determination of vascular reactivity has been termed Digital Temperature Monitoring (DTM) by certain of the present inventors. In one standard utilization, DTM employs a standard arm-cuff vascular reactivity procedure, which includes a temporary occlusion of blood flow in the arm. During the cuff occlusion, the lack of blood flow (ischemia) elicits a microvascular dilative response (opening small vessels). Upon releasing the cuff, blood flow rushes into the forearm and hand, not only restoring baseline flow but also resulting in an overshoot (reactive hyperemia). This overshoot causes shear stress in the larger (conduit) arteries, which stimulates these arteries (macrovessels) to dilate and accommodate the increased blood flow.

A sensitive fingertip temperature sensor monitors, records, and analyzes fingertip temperature during the above cuff occlusion and release procedure. Temperature changes serve as a surrogate marker of blood flow changes that result from vascular reactivity. In one embodiment of the DTM procedure, an automated procedure is initiated beginning with an automated blood pressure measurement, followed by cuff occlusion of the right arm. During the cuff occlusion (2 to 5 minutes), fingertip temperature in the right hand falls because of the absence of warm circulating blood. Once the cuff is released, blood flow rushes into the forearm and hand, causing a temperature rebound (TR) in the fingertip which is directly proportional to the vascular reactivity. The higher the temperature rebound (TR), the better the vascular reactivity.

Figure 3A:
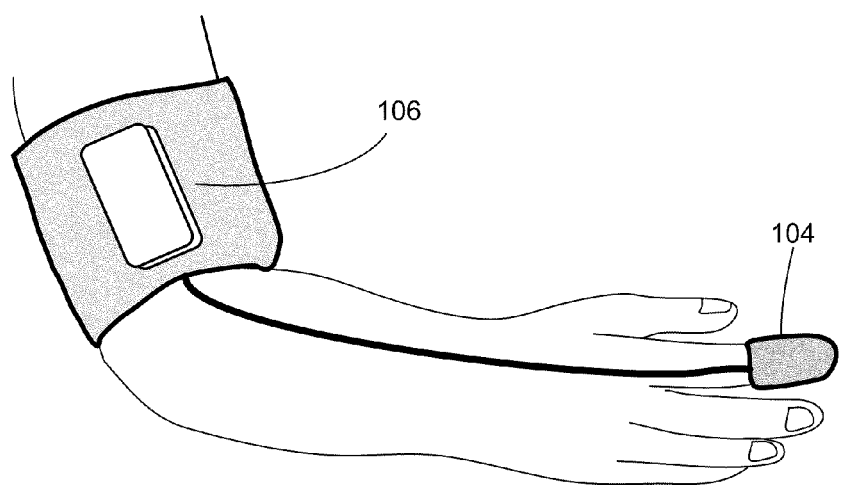
FIG. 3a depicts an occlusive arm band or cuff in which cuff inflation and deflation can be controlled by a device mounted externally on the cuff and includes a fingertip monitor of induced ischemia.
Figure 3B:
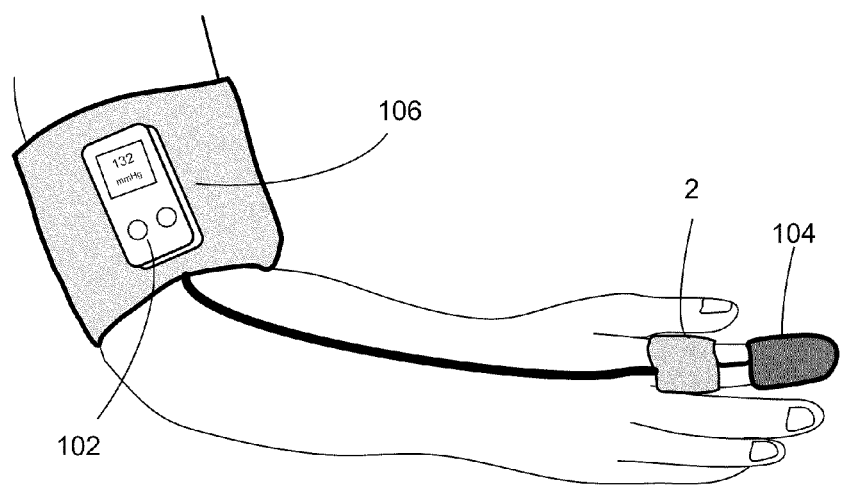
FIG. 3b depicts a system for monitoring the induced ischemia by a fingertip probe that transmits information to the cuff control device and includes a finger mounted artificial pulse generator and pulse oximetry detector.

FIGS. 2 and 3a depict use of fingertip monitor (104) in conjunction with a blood flow occlusive device (106) located on an upper or lower extremity. In the depicted embodiment of FIG. 3a, the fingertip monitor is a DTM that monitors fingertip temperature in conjunction with induced reactive hyperemia in order to provide a surrogate marker of vascular reactivity as a result of repeated ischemic conditioning. In the depicted embodiment of FIG. 3b, an artificial pulse generator (2) is included to provide an artificial pulse and fingertip monitor (104) is, or includes, a pulse oximeter. In one embodiment the pulse generator (2) effects mechanical actuation by pulsating fluid pressure in a cuff to cause mechanical disturbance of arterial blood. In other versions, repetitive, external electromechanical actuation provides the artificial pulse. In still other versions, the artificial pulse is generated by external non-mechanical optical illumination utilized to imitate the absorption patterns of a pulsatile blood flow signal by oscillating the intensity of a light source of either a single or multiple wave length. The optional extremity mounted monitor (102) is adapted to display one or more of program parameters, ambient temperature, blood pressure, DTM parameters of fingertip temperature over time, and pulse oximetry data.

In one embodiment, the method for monitoring the vascular or neurovascular response further includes simultaneously measuring and recording additional physiologic parameters including pulse rate, blood pressure, galvanic response, sweating, core temperature, and/or skin temperature on a thoracic or truncal (abdominal) part.

In one alternative embodiment, local ischemia of the superficial skin layers is provided by an inflatable mitten, sock or glove that operates to provide compression against the skin and thus restrict normal blood flow to the superficial tissues. As with ischemia induced by blockage of blood flow by compression over an artery such as by inflation of a blood pressure cuff, the induction of superficial pressure can be implemented according to a schedule of transient induced pressure as the treatment or conditioning requires. Several other embodiments for inflatable compression are possible such as for example a full body suit that can be used to provide ischemia to the superficial skin layers.

Prevention and Treatment of Hypertension

Chronic medical conditions have various degrees of severity in different individuals including periods of partial remission and recrudescence. However, because each condition cannot be predicted and has variations for different patients, the ischemic conditioning therapy of the present invention can be modified to suit the unique parameters for the particular condition and patient. The present method of administering one or more transient ischemic episodes to one or more limbs according to a schedule is neither dangerous nor expensive and may be readily implemented in every patient. In one embodiment, cuffs are placed on both arms and legs for ischemic conditioning in the treatment of hypertension. The device can be implemented for either in-patient or, preferably, outpatient treatment. The transient ischemic episodes provide protection and treatment against chronic medical conditions by several mechanisms including without limitation: increased nitric oxide bioavailability, increased scavenging of free radicals and reduction of inflammation. If administered in a series of episodes over a sufficiently amount of time, the method is expected to increase vasodilative capacity including by increased arterial and smooth muscle flexibility, as well as increases in functional capillary density, and may be further expected to hasten wound healing.

In an embodiment of the invention, a scheduled series of transient ischemic episodes is applied as conditioning to prevent or manage chronic hypertension. Of the numerous compounds that are released following an ischemic episode as described herein, several are known to have anti-hypertensive effects. For example, increases in nitric oxide and adenosine bioavailability are known to occur after an ischemic episode. These compounds are frequently targeted by drug therapies and are well known to relax smooth muscle cells, decrease arterial stiffness, and improve hypertension over time.

In an embodiment, episodes of transient ischemic conditioning are employed to improve monitoring of stages of hypertension by vascular reactivity measurements. For example, since healthy individuals are expected to have an increase in vascular reactivity by vasodilation upon an ischemic episode, healthy patients can show a decrease in blood pressure following ischemic conditioning. Hypertensive patients can be expected to have limited vasodilation capacity and thus have unchanged or even increased blood pressure after an ischemic conditioning treatment. In an embodiment, any vascular reactivity measurement that is suitable for the methods described herein can be used to determine stages of hypertension by ischemic conditioning. In an embodiment, utilizing ischemic conditioning to characterize stages of hypertension does not significantly affect heart rate of the patient. This creates an advantage over the increased heart rate problem faced by many exercise-induced ischemic vascular reactivity measures such as treadmill stress testing. Thus, ischemic conditioning is able to simulate ischemic effects of exercise but avoid associated problems.

In an embodiment, other chronic medical conditions can also benefit from scheduled ischemic conditioning and the resulting increase in perfusion, relaxation of smooth muscle cells, vasodilation, and elaboration of anti-inflammatory and anti-oxidant mediators. For example, microvascular dilative capacity is hindered and inflammation is increased in Raynaud's syndrome and several associated disorders such as scleroderma (a collagen-related immune disorder) and small vessel vasculitis (including vasculitis associated with anti-neutrophil cytoplasmic antibodies, or ANCAs). Further, diabetes, insulin resistance, high blood glucose, and several other metabolic disregulations are well known to exacerbate inflammation and oxidation. Even further, patients with chronic coronary conditions that reduce ejection fractions and perfusion can benefit from the effects of ischemic conditioning. For example, chronic coronary heart disease patients, heart failure (especially the more severely symptomatic such as in Class III and IV patients), ischemic heart, and stable angina can exhibit chest pain upon exercise which limits the capacity for physical conditions. However, these patients can receive similar benefits of exercise by episodes of ischemic conditioning. Physical conditioning the extent tolerable is expected to increase the benefits of the ischemic conditioning provided herein.

In an embodiment, ischemic conditioning can allow for detection and management of subclinical diabetic neuropathy. Comparing nerve conduction differences before and after an episode of ischemic conditioning can provide information about existence and amounts of nerve damage due to diabetic microvascular injury. Any suitable nerve function measurement, such as needle electromyography (EMG), can be used.

Intermittent Heating for Protection and Treatment

In an alternative embodiment, increased blood flow, enhanced metabolic activity, and anti-oxidant capability is obtained by intermittent heating of the hands and/or feet, or digits thereof. Heat is employed to shift the sympathetic-parasympathetic balance, including through the induced increase in local production of nitric oxide, in order to induce vasodilation and reduced resistance to peripheral blood flow.

In certain embodiments, the heat is provided by a wearable appliance that includes a heating element, a heating controller connected to the heating element, and a source of power for the heating element. As used herein, the term "wearable appliance" includes heatable inserts or pads that are dimensioned for placement in desired anatomical locations, including stand-alone appliances, appliances disposed in garments, and appliances that are used in association with a garment. Appliances that are used in association with a garment include appliances that are worn inside and those that are worn outside of the garment. As used herein, the term "non-wearable" appliance includes fixtures and/or portable devices that are not dimensioned to be attached or carried by an individual during ambulation.

In certain embodiments, a wearable treatment appliance is provided that is dimensioned to be worn as mittens, socks or booties, or gloves. The heating applied must be of sufficient magnitude to cause vasodilation. The optimal site for heating, as well as the intensity and duration of heating, can be readily determined for a given individual based on whether or not the desired vasodilation is obtained.

In one embodiment, local administration of heat is chronic, regular or periodic for a period prior to episodes of ischemic conditioning. For example, the individual patient may schedule a pattern of heating, such as for limited periods 2-10 times a day for a period preceding each round of ischemic conditioning. In another embodiment, heat is administered to the future site for a period prior to ischemic conditioning. Depending on responses desired and obtained in the individual patient, the intensity and duration of heat can be tuned for optimal responses.

In one embodiment of the invention, the heating is provided by Far Infrared Radiation (FIR). FIR is centered around a wavelength of 100 μm on the electromagnetic spectrum. Commercially available versions of such elements able to provide heat to subcutaneous tissue include, for example, FIR Radiant Heating elements. (Challenge Carbon Technology Co., Taiwan). Such elements are suited for FIR heated clothing due to their flat form and foldable, durable and washable properties. The elements as provided for use in clothing include lithium-ion batteries, temperature controller and OCP (Over-Charge Protector) integrated in one controller that provides for rapid heat up according to set upper levels.

Combination Therapies

In one embodiment of the invention, at least one ischemic conditioning treatment of induced ischemia or hypoxia and/or application of heat is combined with pharmacotherapy including by administration of an anti-hypertensive agent, vasodilating agent, anti-oxidant, and/or anti-inflammatory agent. Multiple compounds are known in each of these categories. Existing vasodilators include for example hydralazine, ACE inhibitors (such as for example enalapril), alpha-beta blockers (such as for example carvedilol), minoxidil, and calcium channel blockers (such as for example nisoldipine, nifedipine, diltiazem and verapamil). New vasodilators such as, for example, oxdralazine are being developed and may be equally suitable. Pharmacotherapy includes agents that increase the local bioavailability of NO. The pharmacotherapy can be administered systemically or locally, such as by iontophoresis.

In another embodiment, at least one ischemia conditioning treatment of induced ischemia or hypoxia, and/or application of heat, is combined with non-pharmacologic techniques for modulating the autonomic nervous system (ANS), mostly for regional and transient modulation based on anatomical reflex zones. These non-pharmacologic techniques may include non-invasive electric, magnetic, or electromagnetic neuromodulating devices used to increase local ANS activity. In another embodiment, transient intermittent ischemia and or heating is combined with hand exercises to increase demand and thereby improve nitric oxide bioavailability in the target areas.

Improving Metabolic Endurance and Athletic Performance

In one embodiment of the invention, metabolic endurance and athletic performance can be improved by repeated, scheduled ischemic conditioning treatments. Such treatments provide a natural stimulus for the metabolic machinery (mitochondrial activity, intracellular genes, mRNA, proteins) of the ischemic tissue to better adapt itself to anaerobic conditions, such as those encountered during prolonged exercise and continuous, strenuous activity. Repeated ischemic conditioning treatments are expected to induce metabolic changes and adaptation similar to that induced by exercise conditioning. Ischemic conditioning modulates the supply component, whereas exercise conditioning modulates the demand component. The intracellular metabolic machinery responds to the balance between supply and demand for oxygen and other required nutrients. A decrease in supply (ischemia) or an increase in demand (exercise) will trigger a similar response.

Artificial Pulse Oximetry

Pulse oximetry is a non-invasive method allowing the monitoring of the oxygenation of a patient's hemoglobin. A sensor is placed on a thin part of the patient's anatomy, usually a fingertip or earlobe, and a light containing both red and infrared wavelengths is passed from one side to the other. Changing absorbance of each of the two wavelengths is measured, allowing determination of the absorbances due to the pulsing blood. Based upon the ratio of changing absorbance of the red and infrared light caused by the difference in color between oxygen-bound (bright red) and oxygen unbound (dark red or blue, in severe cases) blood hemoglobin, a measure of oxygenation (the percent of hemoglobin molecules bound with oxygen molecules) can be made.

Existing methods of pulse oximetry require a naturally occurring pulsatile signal in order to function. Standard pulse oximetry will not function correctly in the absence of pulsatile blood flow or during low perfusion states, such as during surgery, hypovolemic shock, cardiogenic shock, septic shock, etc.

In one embodiment of the invention, artificial pulse oximetry can be used to measure oxygen saturation of blood hemoglobin (% $SpO_2$) in the absence of naturally occurring pulsatile blood flow (e.g., surgery with heart bypass pump, circulatory shock, occlusive arterial disorders, etc.) in humans and animals. Artificial pulses can simulate natural pulsatile blood flow in order to enable pulse oximetry devices to calculate arterial and capillary oxygen saturation. This method may also use physiological signals detected by devices such as electrocardiograms to simulate the natural pulsatile rhythm.

In another embodiment, the artificial pulsatile signals are generated by either external mechanical actuation that causes oscillatory displacement of blood or external non-mechanical optical illumination. Methods of generating an artificial pulsatile signal include, but are not limited to, the following:

Pulsating fluid pressure in a cuff to cause mechanical disturbance of arterial blood.

Repetitive, external electromechanical actuation

Repetitive, self-induced physical motion

Optical illumination to imitate the absorption patterns of a pulsatile blood flow signal by oscillating the intensity of a light source (single or multiple wave length)

Figure 4A:
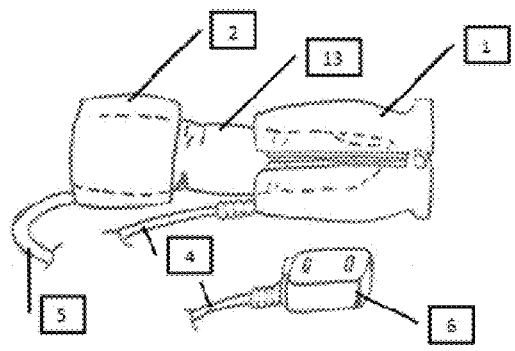
FIG. 4a depicts a conventional finger pulse oximeter and reflectance oximeter sensor.

FIG. 4a depicts a conventional finger pulse oximeter (1) and reflectance oximeter (6) sensor. A finger cuff (2) is placed on the proximal section of the finger and its pressure is increased to supra-systolic by monitoring when the pulse oximeter loses signal. Once at this supra-systolic level, its pressure is oscillated via the fluid tube (5) to create an artificial flow in the distal portion of the fingertip. This flow is detected by the pulse oximeter and reported to an interpreting device (8) which displays the saturated oxygen during an occluded or low flow state.

Figure 4C:
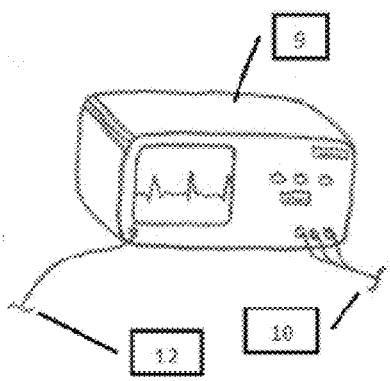
FIG. 4c depicts an embodiment of the external illumination source that takes its input from an external physiological signal detector such as the ECG device in FIG. 4d.
Figure 4B:
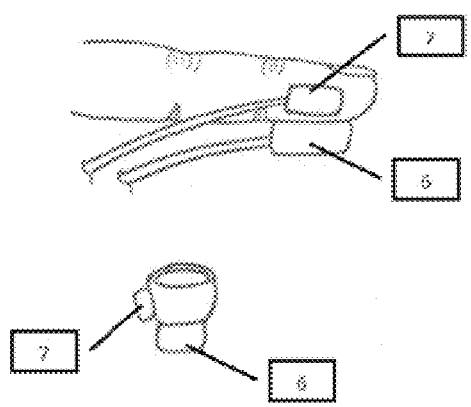
FIG. 4b depicts a method that involves using external optical illumination to imitate the absorption patterns of pulsatile blood.
Figure 4D:
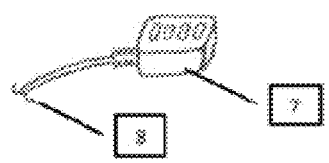
FIG. 4e depicts and embodiment of the device that uses an external electromechanical actuator to cause oscillatory displacement of blood in the underlying blood vessels. These oscillations are detected by the SpO$_2$ sensor and reported during a low or no flow state.
Figure 4E:
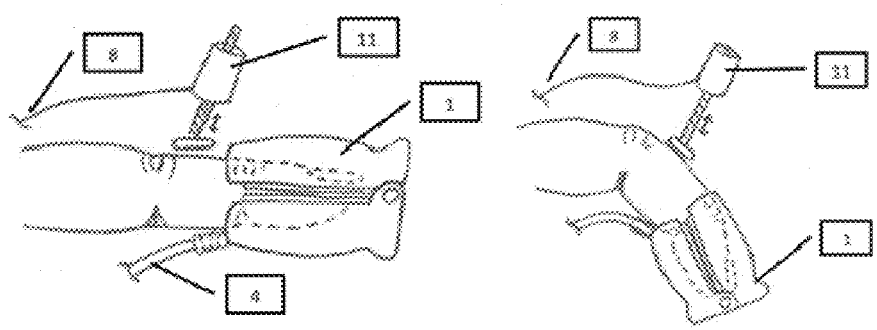

FIG. 4b depicts a method that involves using external optical illumination (7) to imitate the absorption patterns of pulsatile blood. The pulse oximeter sensor (6) is able to detect this pulsatile fluctuation in light intensity and report saturated oxygen in a low or no flow state. FIG. 4c depicts an embodiment of the external illumination source (7) that takes its input (8) from an external physiological signal detector such as the ECG device (9) in FIG. 4d. The ECG electrodes (10) attain the patient's heart rate, for example, and send an output signal (12) to the light source or any electromechanical actuator. FIG. 4e depicts and embodiment of the device that uses an external electromechanical actuator (11) to cause oscillatory displacement of blood in the underlying blood vessels. These oscillations are detected by the $SpO_2$ sensor (1) and reported during a low or no flow state.

In another embodiment, this method can also be used with existing pulse oximetry sensors during conditions of low pulse amplitude or non-pulsatile flow by programming the device to initiate artificial pulsations whenever pulsatile blood flow is absent. The artificial pulsations will create an interpretable signal and allow the pulse oximetry device to continue to measure blood oxygen saturation.

Although particular embodiments of the present invention have been shown and described, it should be understood that the above discussion is not intended to limit the present invention to these embodiments. One skilled in the art will readily appreciate that various changes and modifications may be made without departing from the spirit and scope of the present invention. Thus, the present invention is intended to cover alternatives, modifications, and equivalents that may fall within the spirit and scope of the present invention as defined by the claims.

We claim:

1. A method for improving metabolic endurance and athletic performance by repeated ischemic conditioning treatments comprising:
   a) measuring one or more baseline hemodynamic parameters of a subject,
   b) applying an ischemic treatment in the subject adapted to improve endurance and athletic performance by occluding and releasing arterial flow using a blood flow occlusive device in one or more extremities of the subject on a repeated basis,
   c) measuring post-ischemic parameters in the subject, d) using a computer to compare the baseline and post-ischemia parameters, and
e) using a computer to provide an assessment of the ischemic conditioning treatment over time.

2. The method of claim 1, further comprising measuring blood oxygen saturation during ischemia using an artificial pulse together with oximetry to improve assessment of the ischemic conditioning treatments.

3. The method of claim 2, wherein the artificial pulse is generated by mechanical actuation.

4. The method of claim 3, wherein the mechanical actuation is affected by pulsating fluid pressure in a cuff to cause mechanical disturbance of arterial blood, repetitive, external electromechanical actuation, or repetitive, self-induced physical motion.

5. The method of claim 2, wherein the artificial pulse is generated by external non-mechanical optical illumination utilized to imitate the absorption patterns of a pulsatile blood flow signal by oscillating the intensity of a light source of either a single or multiple wave length.

6. A metabolic endurance and athletic performance improving device comprising an external cuff system for suprasystolic arterial occlusion and reperfusion; a control device for controlling compression and release of elements in accordance with a schedule for repeated, ischemic conditioning treatments comprising a repeated combination of occluding suprasytolic blood flow and releasing blood flow for improved metabolic endurance and athletic performance.

7. The device of claim 6 further comprising a pulse oximeter.

8. The device of claim 7 further comprising an artificial pulse generator wherein the pulse oximeter is adapted to measure blood oxygenation in an artificial pulse created by the artificial pulse generator.

9. The device of claim 6 wherein a drop in finger tip skin temperature is a marker of ischemia.

10. A method for improving endurance and athletic performance comprising: scheduling an ischemic conditioning treatments comprising occluding arterial blood flow above systolic pressure using a bloodflow occlusive device, causing reperfusion by releasing the blood flow occlusive device; and repeating the ischemic condition treatment.

11. The method of claim 10, wherein the program of ischemic conditioning comprises at least 2 cycles of from about 2 to about 15 minutes of occlusion on at least one extremity followed by reperfusion.

12. The method of claim 11, wherein the program of ischemic conditioning comprises at least 2 cycles of from about 2 to about 5 minutes of occlusion.

13. The method of claim 11, wherein the program of ischemic conditioning comprises a plurality of cycles of occlusion followed by reperfusion within 24 hours of an athletic event.

14. The method of claim 10, wherein the ischemic conditioning is applied to one or more extremities using an external cuff system for arterial occlusion.

15. The method of claim 10 wherein the ischemic conditioning program is personalized based on monitoring the level of ischemia.

16. The method of claim 15 wherein the level of ischemia is measured using an artificial pulse oximeter.

17. The method of claim 10, wherein the ischemic conditioning is applied to one or more extremities using external pressure using a pressurizable garment.

18. The method of claim 10 wherein ischemic conditioning treatments are provided during physical activity or exercise.

* * * * *